US00PP34493P2

(12) United States Plant Patent
Dutt

(10) Patent No.: US PP34,493 P2
(45) Date of Patent: Aug. 16, 2022

(54) FINGER LIME PLANT NAMED 'UF SUNLIME'

(50) Latin Name: ***Citrus inodora* x *Citrus australasica* var. *sanguinea***
Varietal Denomination: UF SunLime

(71) Applicant: Florida Foundation Seed Producers, Inc., Marianna, FL (US)

(72) Inventor: Manjul Dutt, Marianna, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 17/300,785

(22) Filed: Nov. 5, 2021

(51) Int. Cl.
*A01H 5/08* (2018.01)
*A01H 6/78* (2018.01)

(52) U.S. Cl.
USPC ..... Plt./201

(58) Field of Classification Search
USPC ..... Plt./201, 202
See application file for complete search history.

(56) References Cited

PUBLICATIONS

Bowman, Kim D. et al., "Minnie Finger Lime: A New Novelty Citrus Cultivar," HortScience, vol. 54(8), 1425-1428 (Aug. 2019) (available online at https://journals.ashs.org/hortsci/view/journals/hortsci/54/8/article-p1425.xml).

*Primary Examiner* — Susan McCormick Ewoldt
(74) *Attorney, Agent, or Firm* — Katherine Koenig; Koenig IP Works, PLLC

(57) ABSTRACT

A new and distinct hybrid cultivar of finger lime plant named 'UF SunLime', characterized by precocious bearing trees containing intense red-colored, cylindrical-shaped fruits with a blunt protuberance on both ends and dark red ovoid to pyriform juice vesicles that detach easily from the locules. 'UF SunLime' produces annual crops of well-colored deep red fruit that do not require prolonged cold induction to express anthocyanin both internally and externally under Central Florida conditions. Both the rind and juice vesicles have enhanced anthocyanin accumulation. Additionally, the rind of 'UP SunLime' contains oil glands, and pleasantly fragrant oil can be released during cutting, especially with recently harvested fruit.

6 Drawing Sheets

Genus and species: *Citrus inodora* x *Citrus australasica* var. *sanguinea.*

Cultivar denomination: 'UF SunLime'.

CROSS-REFERENCE TO RELATED APPLICATIONS

N/A.

ACKNOWLEDGEMENT OF FEDERAL RESEARCH SUPPORT

N/A.

BACKGROUND OF THE NEW CULTIVAR

Finger lime is a *Citrus* fruit that is native to the sub-tropical rainforests of Australia. Finger limes are grown throughout tropical and sub-tropical climates worldwide, although commercial production is currently small compared to other types of *Citrus*. However, popularity of finger limes, which are sometimes called "*Citrus* caviar," is on the rise, particularly in the hospitality and restaurant industries because of the unique large and detached vesicles within the fruit. Finger lime also makes an excellent potted plant or hedge if carefully pruned. Finger lime scions are typically grafted onto desirable rootstocks. Additionally, finger limes are sexually compatible with other types of *Citrus*, which has led to the development of hybrids.

The present invention relates to a new and distinct hybrid cultivar between two Australian lime species (*Citrus inodora* x *Citrus australasica* var. *sanguinea*) designated 'UF SunLime'. The new hybrid cultivar can be distinguished by its precocious bearing trees containing intense red-colored, cylindrical-shaped fruits with a blunt protuberance on both ends and dark red ovoid to pyriform juice vesicles that detach easily from the locules.

'UF SunLime' was derived from a seedling tree that was itself selected from a population of hybrids produced from a cross performed at Lake Alfred, Fla., in the spring of 2012. The seed parent was an open pollinated *Citrus inodora* clone '80-527A' seedling (Russell River lime or large leaf Australian wild lime; unpatented). The pollen parent was the *Citrus australasica* var. *sanguinea* 'DPI 50-36' (a variety of Australian finger lime having red pulp; unpatented). The original seedling tree was budded onto 'Carrizo' citrange rootstock in February 2013 and planted in the field in October 2013. Fruits were first selected during the autumn of 2018. 'UF SunLime' was also asexually propagated in March 2019 on several different rootstocks, including 'Volkamer' lemon, 'Rough Lemon', 'Carrizo' citrange, and 'Swingle' citrumelo, and planted in different locations in Homestead, Fla., and Immokalee, Fla.

Plant Breeder's Rights for this cultivar have not been applied for. The new hybrid cultivar 'UF SunLime' has not been made publicly available more than one year prior to the filing of this application.

SUMMARY OF THE INVENTION

'UF SunLime' produces annual crops of well-colored fruit that do not require prolonged cold induction to express anthocyanin both internally and externally under Central Florida, conditions. The main flowering occurs during late February to March with sporadic flowering throughout the year. Thus, mature and immature fruit can be observed at the same time in the tree. The main crop matures between December and January in Lake Alfred, Fla. (USDA Zone 9), but fruits can be harvested well into April. Fully mature fruit do not hold on to the tree and should be periodically harvested during the season as they mature. Both the rind and juice vesicles (the *Citrus* "caviar" of commerce) have enhanced anthocyanin accumulation (Table 1). 'UF SunLime' is also morphologically distinct from both parent varieties. The *Citrus inodora* clone '80-527A' seedling female parent produces an elongated fruit that does not produce anthocyanins. Fruits at maturity remain yellow-green in color. The *Citrus australasica* var. *sanguinea* 'DPI 50-36' pollen parent produces a similar-shaped but smaller fruit with poor internal color and with a less pleasant flavor. The rind of 'UF SunLime' contains oil glands, and pleasantly fragrant oil can be released during cutting, especially with recently harvested fruit. A 6-year-old mature tree can produce approximately 150 fruits. Trees have been observed to grow quite well even under endemic huanglongbing (HLB) disease conditions, but it is too early to determine the actual level of HLB tolerance.

TABLE 1

Table 1. Total average anthocyanin content (mg C3GE/kg FW) in 'UF SunLime' fruits under central Florida growing conditions.

| | Peel | Pulp |
|---|---|---|
| Fully mature fruit | 7.1 | 3.2 |

The new cultivar 'UF SunLime' has been reproduced asexually through vegetative cuttings and has been found to retain its distinctive characteristics through successive asexual propagations. The new cultivar 'UF SunLime' was first propagated asexually by grafting vegetative budwood obtained from the original seedling tree on six-month-old 'Carrizo' citrange rootstock in the spring 2013 and planted in the field during the fall of 2013 in Lake Alfred, Fla. No phenotypic or genotypic variants have been observed from plants that resulted from this asexual propagation.

The new finger lime hybrid cultivar 'UF SunLime' has not been observed under all possible environmental conditions. The phenotype of the new hybrid cultivar may vary with variations in environment and cultural practices such as temperature, light intensity, fertilization, irrigation, and application of plant growth regulators without any change in genotype.

DESCRIPTION OF THE FIGURES

'UF SunLime' is illustrated by the accompanying photographs, which show the tree's form, foliage, and fruit. The colors shown are as true as can be reasonably obtained by conventional photographic procedures. Colors in the photographs may differ slightly from the color values cited in the detailed botanical description, which accurately describe the colors of the new finger lime hybrid cultivar.

DETAILED BOTANICAL DESCRIPTION OF THE CULTIVAR

Figure 1:
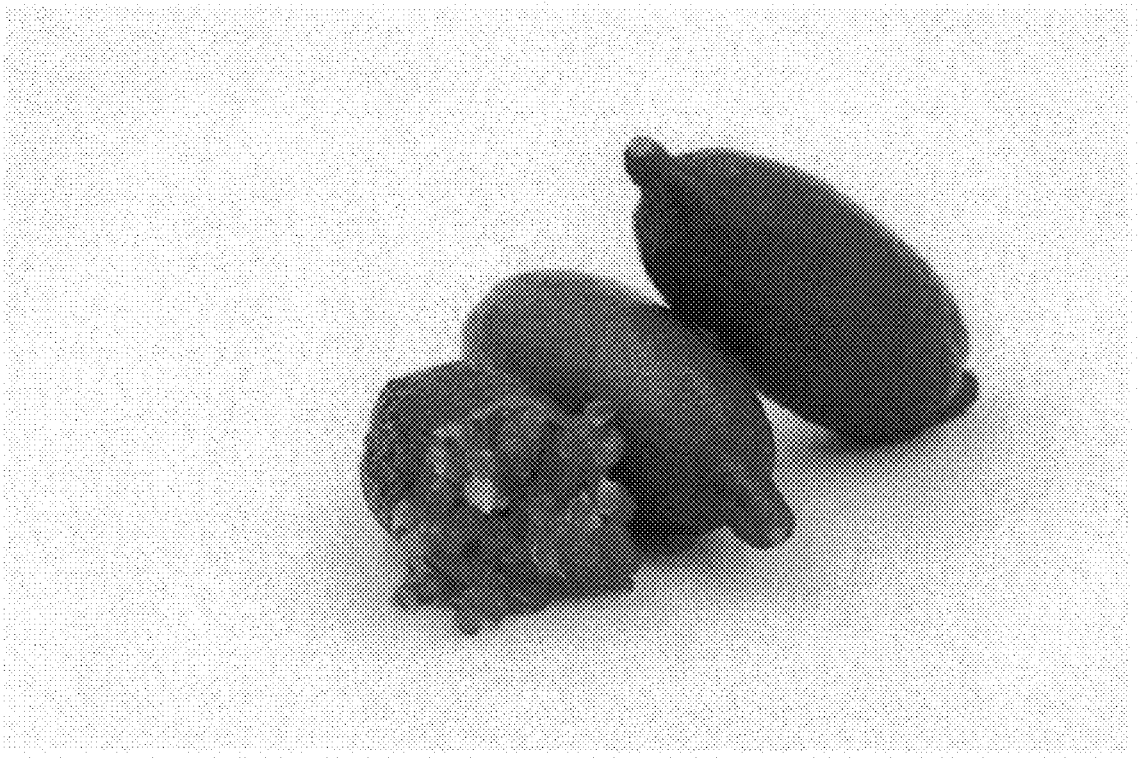
FIG. 1 shows a close-up view of mature fruit, both with the rind intact and with the fruit cut open (cross-sectional view) to show juice vesicles within.
Figure 2:
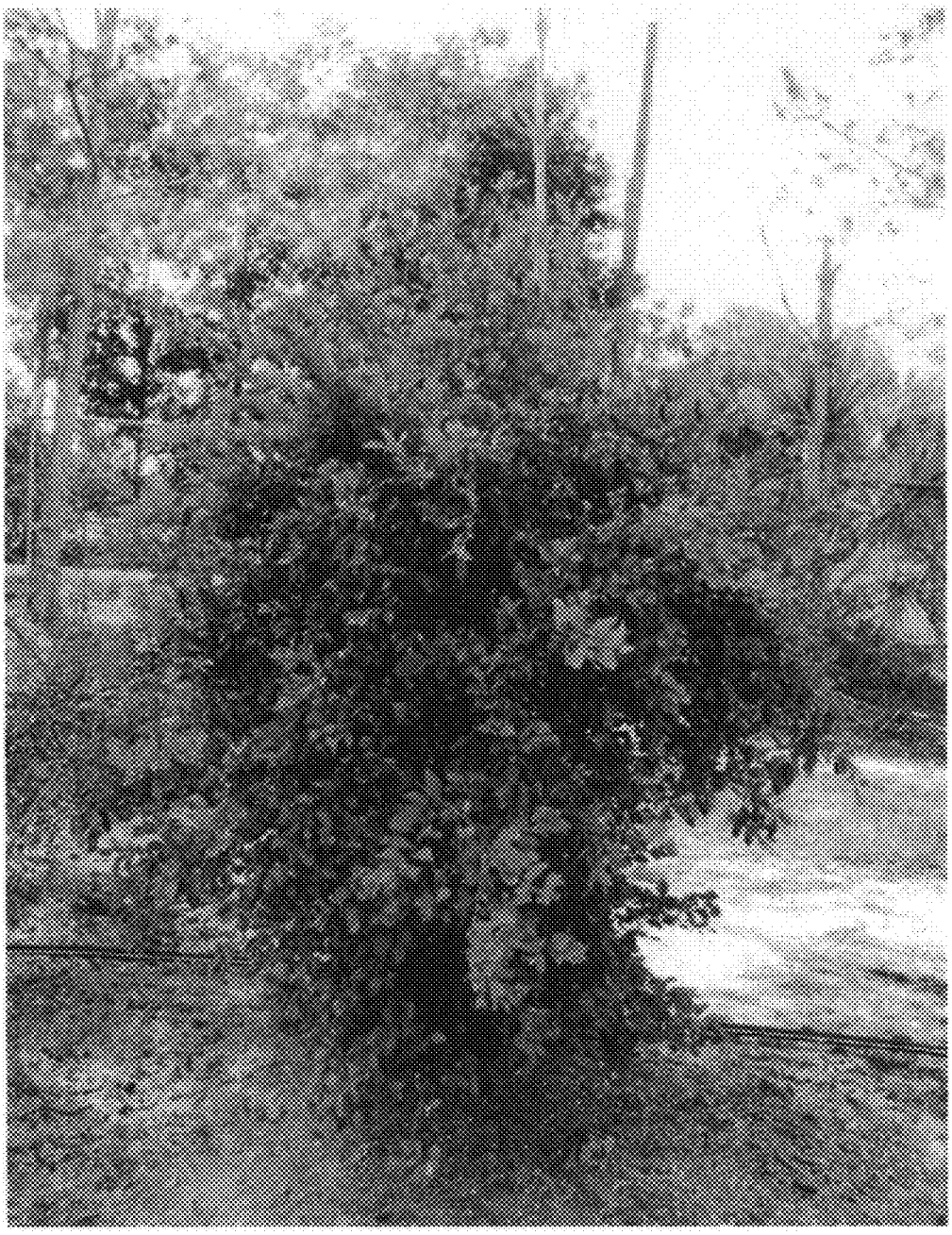
FIG. 2 shows the overall mature plant growth habit in late summer.
Figure 3:
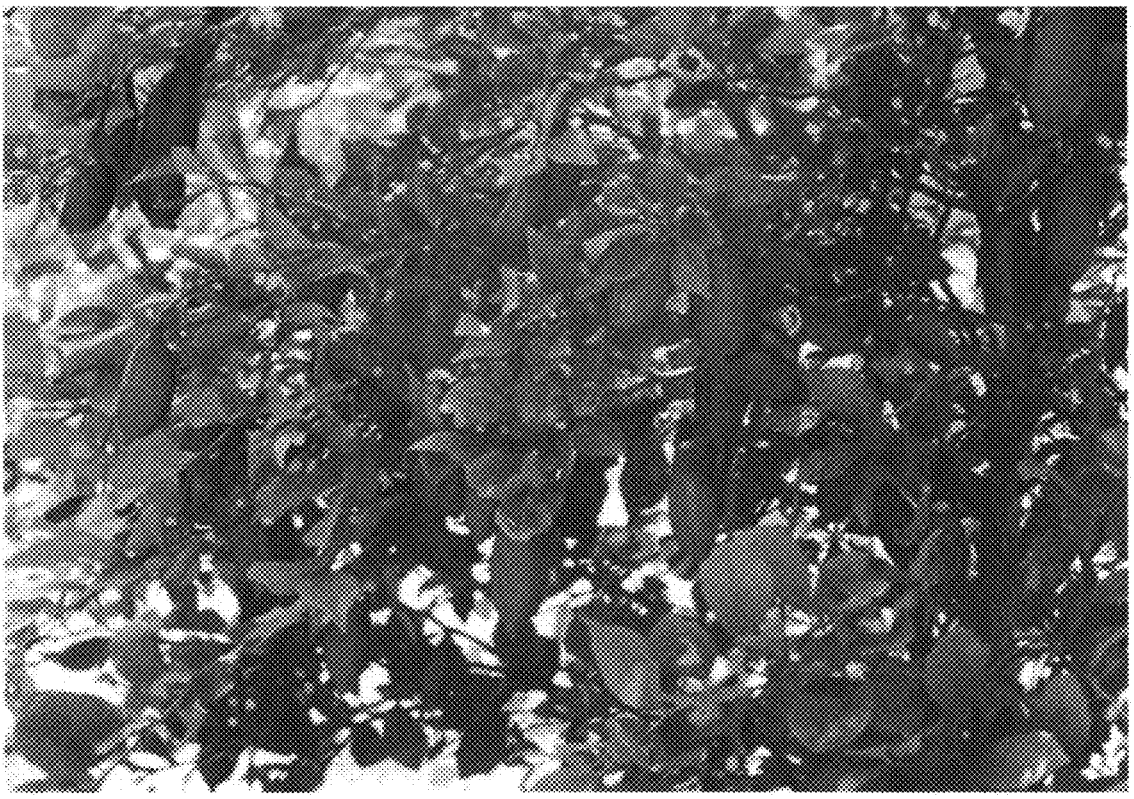
FIG. 3 shows mature fruits hanging on the tree.
Figure 4:
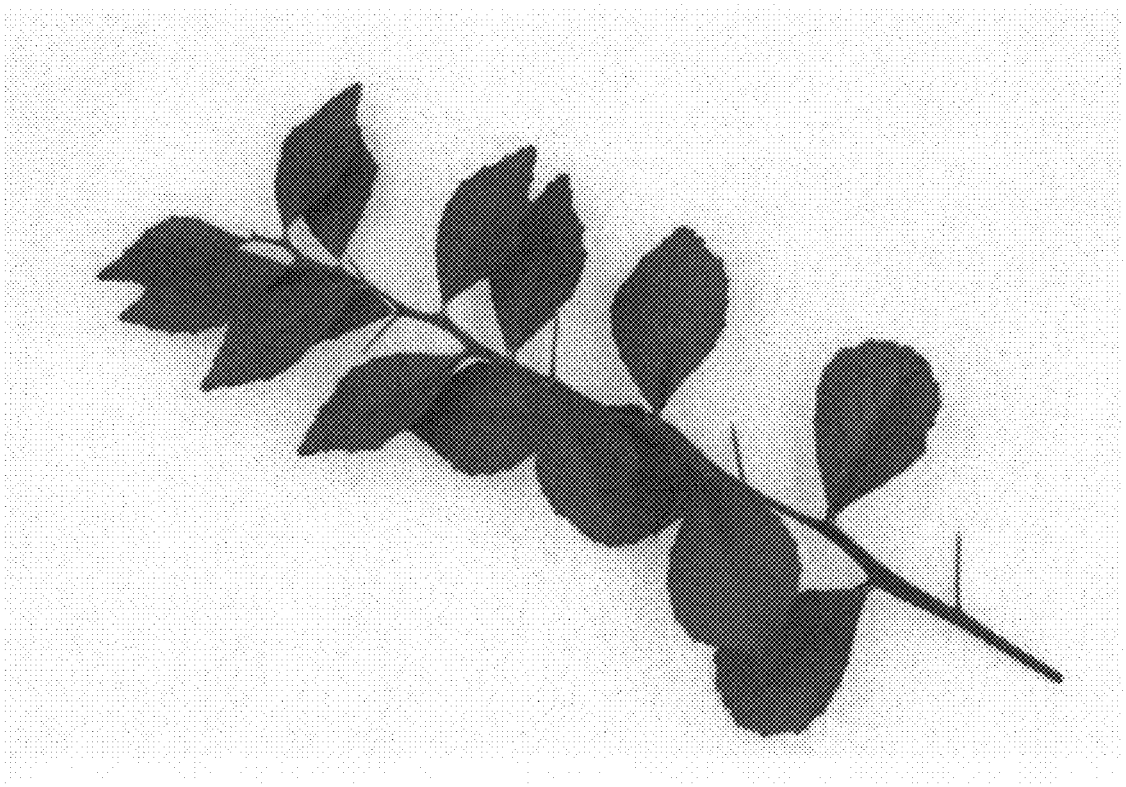
FIG. 4 shows a close-up view of mature leaves.
Figure 5:
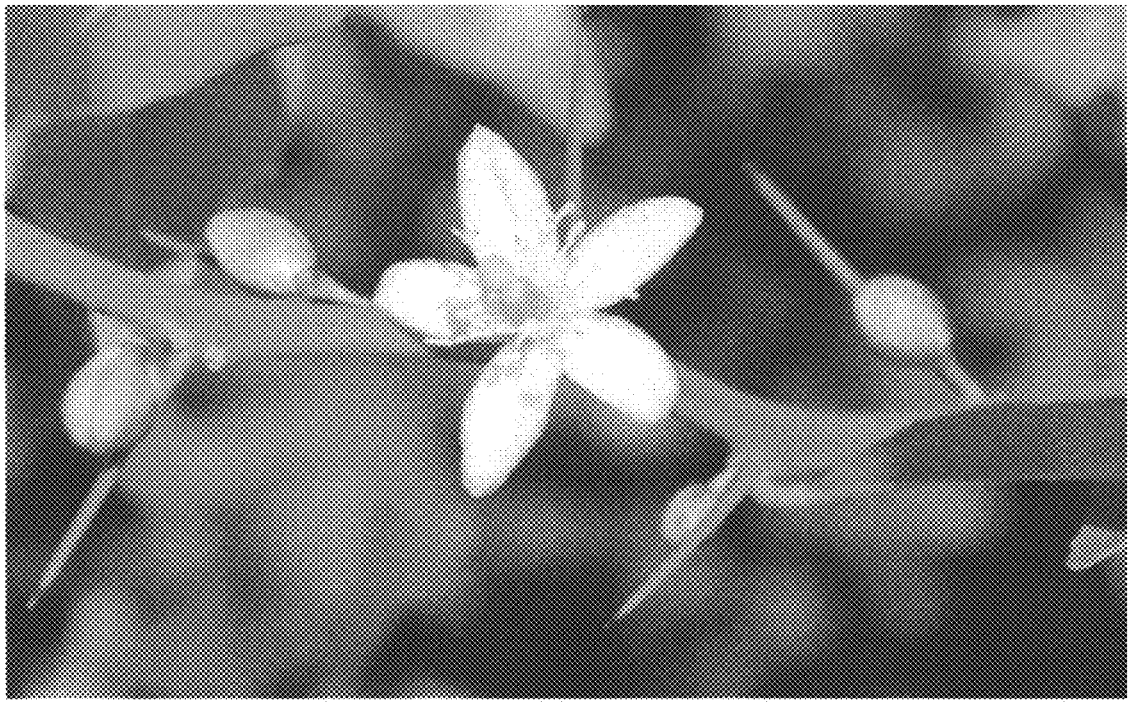
FIG. 5 shows a close-up view of an open flower and unopened flowers.
Figure 6:
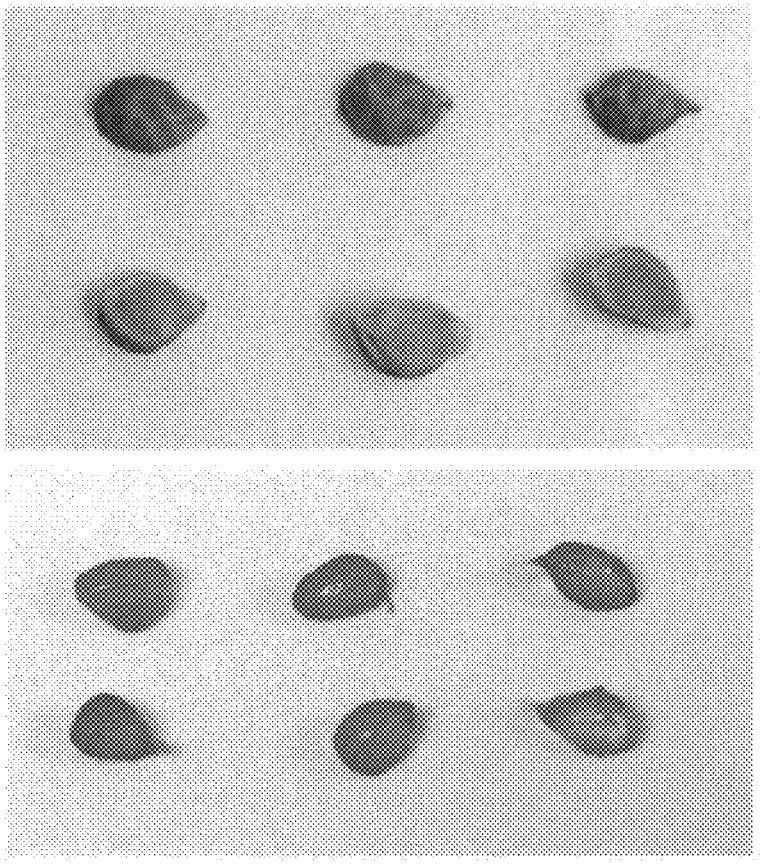
FIG. 6 shows a close-up view of the seeds (top) and juice vesicles (bottom) obtained from mature fruit.

The following detailed description sets forth the distinctive characteristics of 'UF SunLime'. The present botanical description is that of the new hybrid cultivar grown as a 6-year-old tree budded onto 'Carrizo' citrange rootstock in Lake Alfred, Fla. Color references are made to The R.H.S. Colour Chart published by The Royal Horticultural Society in London (sixth edition, 2019 reprint). Color descriptions are provided in parentheses.

Botanical Description

Botanical classification:

*Family*.—Rutaceae.

*Botanical name*.—*Citrus inodora* x *Citrus australasica* var. *sanguinea*.

*Common name*.—Finger lime.

*Cultivar*.—'UF SunLime'.

Parentage:

*Female or seed parent*.—Open pollinated *Citrus inodora* clone '80-527A' seedling.

*Male or pollen parent*.—*Citrus australasica* var. *sanguinea* 'DPI 50-36'.

Tree:

*Ploidy*.—Diploid.

*Size*.—Medium small.

*Height*.—2.28 meters.

*Tree spread*.—1.95 meters.

*Vigor*.—Moderately vigorous.

*Density*.—Canopies are moderately dense.

*Form*.—Open-head irregular.

*Growth habit*.—Both upright and lateral growth.

Trunk and branches:

*Trunk diameter*.—8 cm in diameter at 30 cm above ground.

*Trunk texture*.—Smooth.

*Trunk bark color*.—RHS 197A (light olive gray); irregularly striated with RHS 189A (dark yellowish green).

*Crotch angle*.—First crotch forms an angle of about 100 to 110 degrees, middle crotch forms an angle of about 60 degrees.

*Branch length*.—0.78 meters from the first crotch to the tip of the branch.

*Branch texture*.—Relatively rough with small thorns or spines. Thorns can be variable in length and range from 2.5 mm to 15 mm long. Thorns are often paired in younger trees.

*Branch color* (*shoots from previous flush, hardened and 4 mm to 5 mm in diameter*).—RHS 137A (moderate olive green).

Leaves:

*Size* (*lamina average*).—Length: 56.6 mm. Width: 35.2 mm. L/W ratio: 1.6.

*Thickness*.—Greater than typical thickness when compared to other diploid *Citrus* hybrids.

*Type*.—Dimorphic, unifoliate.

*Shape*.—Elliptical to slightly oblanceolate. Apex: Irregularly retuse to emarginate. Base: Acute or acuminate.

*Margin*.—Basal half: Faintly toothed. Apical half: Irregularly crenate or toothed.

*Surface*.—Upper surface (adaxial): Glabrous. Lower surface (abaxial): Pinnately netted venation.

*Arrangement*.—Alternate.

*Color*.—Upper surface (adaxial): RHS 137C (moderate yellowish green). Lower surface (abaxial): RHS 137B (moderate olive green).

*Petiole*.—Shape: Acute, junction between petiole and lamina is articulate. Length: 4.1 mm to 5.9 mm. Width: 0.99 mm to 1.39 mm. Color: RHS 137B (moderate olive green). Anthocyanin coloration in the young leaves: Present.

Flowers and flower buds:

*Type*.—Hermaphrodite.

*Bearing*.—Single flower in leaf axils.

*Flower diameter*.—Fully open flower with average diameter of 22 mm to 25 mm.

*Flower depth*.—Typical flower with average depth of 13.5 mm.

*Flower blooming period*.—February to March, with sporadic blooming throughout the year (for example, a first spring bloom was observed Feb. 25, 2019, and a full spring bloom was observed Mar. 10, 2019).

*Flower bud size*.—Initial visible flower bud: Length: 2.3 mm in length. Diameter: 2.5 mm in diameter. Shape: Round ball shape. Color: RHS 71A (deep purplish red). Mature flower bud: Length: 9.3 mm in length. Diameter: 5.5 mm in diameter. Shape: Subglobose or obovate. Color: RHS 64A (moderate purplish red) with RHS 155B (yellowish white) spots distributed around the flower bud.

*Flower petals*.—Number: 3 to 5. Shape: Oblong shaped. Apex shape: Smooth acute shaped. Base shape: Even obtuse. Color: Abaxial surface with NN155A (yellowish white); adaxial surface with RHS 155C (greenish white) and RHS 64A (moderate purplish red). Margin: Smooth. Length: 9 mm to 12 mm. Width: 5 mm to 6.5 mm. Texture: Soft, smooth.

*Flower sepal*.—Number: 3 to 5 per flower. Shape: Delta shaped with subacute angle at apex. Length: 1.8 mm. Width: 1.5 mm. Apex shape: Subacute angle at apex. Margin: Smooth. Color: Upper surface with RHS 145D (light yellowish green); lower surface with RHS 64A (moderate purplish red).

*Flower pedicel*.—Length: 2.4 mm to 3.5 mm. Diameter: 0.6 mm to 1 mm. Color: RHS 137B (moderate green).

Reproductive organs:

*Fertility*.—Appears self-fertile.

*Stamen length*.—3.95 mm to 6.9 mm.

*Stamen number*.—20 to 25.

*Anther length*.—1.88 mm.

*Anther width*.—0.72 mm.

*Pollen amount*.—Abundant.

*Pistil number*.—1.

*Pistil length*.—7.2 mm to 8.6 mm.

*Style length*.—1.5 mm.

*Style diameter*.—0.7 mm.

*Style color*.—RHS 69D (very pale purple).

*Ovary shape*.—Oval shaped.

*Ovary diameter*.—1.4 mm.

*Ovary color*.—RHS 144C (strong yellowish green).

*Fragrance*.—Fragrant.

Fruit:

*Size*.—Uniform. Length: 71.2 mm on average. Width: 27.5 mm on average.

*Average weight* (*per individual fruit*).—30.4 grams.

*Shape*.—Cylindrical, elongated ellipsoid to slightly fusiform.

*Shape* (*cross-section*).—Round.

*Apex*.—Nipple-shaped protrusion being 5.77 mm (average) in length by 6.48 mm (average) in diameter.

*Base*.—Necked, 5.29 mm in length (average) and 6 mm (average) in diameter.

*Stylar scar*.—Less than 1 mm in diameter and sometimes with remains of persistent style.

*Maturity*.—Fruits mature sporadically throughout the year. The main harvest is between November and February (for example, one harvest occurred between Nov. 15, 2019, to Feb. 15, 2020), although fruit continue to mature until summer.

*Fruit color*.—RHS 185A (deep red). Rind: Adherence: Adherence between albedo (mesocarp) and flesh (endocarp) is weak. The adherence is evenly distributed from base to apex. Thickness: 0.91 mm on average. Texture: Smooth. Color: Flavedo (epicarp): Range between RHS 185A (deep red) to RHS 185B (moderate red). Albedo (mesocarp): RHS 157D (greenish white). Stylar end: Closed. Rind oil cell density: 80-85 oil cells/$cm^2$. Flesh: Number of segments: Average between 5 and 7 segments per fruit. Segment walls: Firm with sufficient strength to maintain integrity as separated. Juice: Moderate. Color: Uniformly RHS 179A (moderate red). Texture: Firm/crunchy. Vesicles: Length: 4.26 mm on average. Diameter (thickness): 2.6 mm on average. Juice index: Soluble solids (average): 8.5 Brix. Acidity (average percent): 8%. Ratio: 1.1. Citric acid: 14.6 mg/L. Malic acid: 10 mg/L. Seeds: Type: Monoembryonic. Number: Ranges from 0 to 10. Shape: Seed shapes are not uniform. Normal seeds are mostly ovoid, usually flattened on one side and often showing small, shallow depression on the other face. Size: Length: 6 mm on average. Width: 2.68 mm on average. Seed coat color: Outer surface: RHS 155B (yellowish white) and wrinkled. Inner surface: RHS 165C (moderate orangish yellow). Cotyledon color: RHS 145D (light yellowish green).

COMPARISON WITH KNOWN CULTIVARS

The new finger lime cultivar 'UF SunLime' can be compared to the finger lime cultivar 'Minnie Finger Lime' (not patented). The new cultivar 'UF SunLime' has deep red fruit with moderate red flesh and average juice acidity of 8%, whereas 'Minnie Finger Lime' has dark green to light green fruit with pale green flesh and average juice acidity of 4.5%-7.2%.

I claim:

1. A new and distinct finger lime plant named 'UF SunLime' as illustrated and described herein.

* * * * *